(12) United States Patent
Cade et al.

(10) Patent No.: US 8,852,631 B2
(45) Date of Patent: Oct. 7, 2014

(54) ACID RESISTANT CAPSULES

(75) Inventors: Dominique Nicolas Cade, Colmar (FR); Xiongwei David He, Colmar (FR)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 13/497,974

(22) PCT Filed: Sep. 14, 2010

(86) PCT No.: PCT/IB2010/054131
§ 371 (c)(1),
(2), (4) Date: Mar. 23, 2012

(87) PCT Pub. No.: WO2011/036601
PCT Pub. Date: Mar. 31, 2011

(65) Prior Publication Data
US 2012/0288562 A1 Nov. 15, 2012

Related U.S. Application Data

(60) Provisional application No. 61/245,392, filed on Sep. 24, 2009.

(51) Int. Cl.
*A61K 9/48* (2006.01)
(52) U.S. Cl.
CPC .................................. *A61K 9/4816* (2013.01)
USPC ............ 424/456; 264/306; 424/451; 514/630
(58) Field of Classification Search
CPC .......................... A61K 9/4816; A61K 2300/00
USPC .................... 424/456, 451; 264/306; 514/630
See application file for complete search history.

(56) References Cited

U.S. PATENT DOCUMENTS

| | | | |
|---|---|---|---|
| 5,264,223 A | 11/1993 | Yamamoto et al. | |
| 5,431,917 A | 7/1995 | Yamamoto et al. | |
| 5,756,123 A | 5/1998 | Yamamoto et al. | |
| 6,294,008 B1 | 9/2001 | Keary et al. | |
| 6,413,463 B1 | 7/2002 | Yamamoto et al. | |
| 6,649,180 B1 | 11/2003 | Matsuura et al. | |
| 2002/0187190 A1 | 12/2002 | Cade et al. | |
| 2003/0072731 A1 | 4/2003 | Gulian et al. | |
| 2003/0175335 A1 | 9/2003 | Scott et al. | |
| 2005/0031853 A1 | 2/2005 | Scott et al. | |
| 2006/0165775 A1* | 7/2006 | Korshak et al. | 424/451 |
| 2007/0043284 A1 | 2/2007 | Sanfilippo | |
| 2010/0233252 A1 | 9/2010 | Tochio et al. | |

FOREIGN PATENT DOCUMENTS

| | | |
|---|---|---|
| DE | 199 26 714 A1 | 8/2000 |
| EP | 0592130 A2 | 4/1994 |
| EP | 1045000 A1 | 10/2000 |
| EP | 1132081 A2 | 9/2001 |
| EP | 1693056 A1 | 8/2006 |
| EP | 1757310 A1 | 2/2007 |
| EP | 2 179 728 A1 | 4/2010 |
| ES | 2 148 114 | 10/2000 |
| JP | 10 291928 A | 11/1998 |
| WO | WO 02/03968 A1 | 1/2002 |
| WO | WO 2004/026284 A1 | 4/2004 |
| WO | WO 2006/043284 A1 | 4/2006 |
| WO | WO 2008/119943 A2 | 10/2008 |
| WO | WO 2009/021377 A1 | 2/2009 |
| WO | WO2009021377 * | 2/2009 ............... A61K 9/48 |

OTHER PUBLICATIONS

Nagata, S.; Title: Advantages to HPMC capsules: A new generation's hard capsule; Drug Delivery Tech.; vol. 2 (2), pp. 34-39, 2002.*
Dhar et al.; Title: Natural Gum Reduced/Stabilized Gold Nanoparticles for Drug Delivery Formulations; Chemistry—A european Journal, vol. 14 (33), pp. 10224-10250; published online Oct. 10, 2008.*
English translation of Spanish Patent Publication No. 2 148 114 published Oct. 1, 2000.
International Search Report dated Nov. 16, 2010 from International Application No. PCT/IB2010/054131.
Office Action dated Feb. 16, 2013 in Chinese Application No. 201080042764.7.
Office Action dated Jan. 23, 2013 in European Application No. 10 759 732.0-2112.
Office Action dated Jun. 5, 2013 from Taiwanese Patent Application No. 099132015.
Ogura, T. et al., "HPMC Capsules—An Alternative to Gelatin", Pharmaceutical Technology International, vol. 11, No. 10, Nov. 1998, entire document.

* cited by examiner

*Primary Examiner* — Johann R Richter
*Assistant Examiner* — Yanzhi Zhang
(74) *Attorney, Agent, or Firm* — Finnegan, Henderson, Farabow, Garrett & Dunner LLP

(57) ABSTRACT

The present invention relates to new acid resistant hard pharmaceutical capsules, a process for their manufacture and use of such capsules particularly but not exclusively for oral administration of pharmaceuticals, veterinary products, food and dietary supplements to humans or animals. The capsules of the invention are obtained by aqueous compositions comprising a water soluble film forming polymer and gellan gum in a mutual weight ratio of 4 to 15 weight parts of gellan gum for 100 weight parts of film forming polymer.

4 Claims, 1 Drawing Sheet

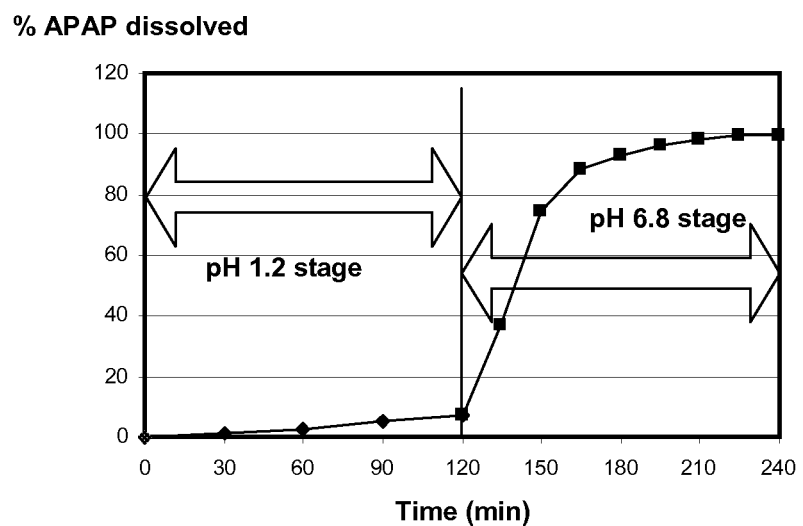

ACID RESISTANT CAPSULES

This application is a national stage entry under 35 U.S.C. §371 of International Application No. PCT/IB2010/054131 filed on Sep. 14, 2010, which claims priority of U.S. Provisional Application No. 61/245,392 filed on Sep. 24, 2009, all of which are incorporated herein by reference.

FIELD OF THE INVENTION

The present invention relates to new acid resistant hard pharmaceutical capsules, a process for their manufacture and use of such capsules particularly but not exclusively for oral administration of pharmaceuticals, veterinary products, food and dietary supplements to humans or animals.

BACKGROUND OF THE INVENTION

Hard pharmaceutical capsules are generally manufactured by using a dip molding process. In this process, pin molds are dipped into an aqueous-based film forming composition. By subsequently gelling the composition adhered on the pins a film is formed. The film is then dried, stripped off the pins and cut to a desired length. Thus, capsules caps and bodies are obtained that can later be filled with a substance and telescopically joined together such that a filled, hard pharmaceutical capsule is obtained. For patent literature disclosing this process one can see e.g. U.S. Pat. No. 5,264,223, U.S. Pat. No. 5,756,123 and U.S. Pat. No. 5,756,123.

Pharmaceutical capsules are widely used in the pharmaceutical field as oral dosage forms for administration to humans and animals. In this context, it is often desirable that the capsules be acid resistant in order to remain intact in the stomach of patients and do not release the encapsulated content therein. Acid resistant capsules are thus useful for the administration of substances instable in an acid environment or substances, like NSAIDs, that are associated with serious gastric side-effects.

Conventionally, the problem of imparting acid resistance to a capsule has been tackled by coating a non-acid resistant capsule with an enteric film. The enteric film comprises well-known acid resistant materials that have a pH-dependent water solubility. Typically, these materials are carboxylic group-containing polymers, such as cellulose acetate phthalate (CAP), hydroxypropyl methylcellulose phthalate (HP-MCP), hydroxypropyl methylcellulose acetate succinate (HPMC-AS), acrylic copolymers and shellac. These materials are water insoluble under gastric conditions (conventionally simulated by pH 1.2) and readily water soluble under intestinal conditions (conventionally simulated by a pH of 6.8).

Drawbacks of the coating solution are typically represented by the complexity and costs of the manufacturing coating process, the high level of expertise needed to effectively perform it, the necessity to perform the coating at the end of the manufacturing cycle, i.e. once the capsules are already filled and, finally, the need for contacting the capsules with solvent-based coating compositions that may leave toxic solvent residues on capsule surface after drying.

Attempts are also known to develop non-coated enteric hard pharmaceutical capsules, i.e. hard capsules whose shells already display gastric resistance and that, as such, do not need any coating step. As of today, satisfactory acid resistant hard capsules can only be obtained by a double dipping method, wherein conventional pins are dipped twice, at least one time in a solution of enteric polymer(s) dissolved in one or more organic solvents. The polymers used in double dipping methods are the same polymers used in conventional coating processes.

The double dipping process needs however specifically developed production equipment which is extremely expensive. Additionally, the problem of using organic solvents in the dipping solution is not overcome which still causes serious concerns about environment and health security.

Thus, there is the need of acid resistant hard pharmaceutical capsules that meet the acid resistance criteria set forth in the major pharmacopoeia, that have satisfactory mechanical performance and that can be manufactured with a cost-effective, environmentally friendly, healthy safe, simple process.

SUMMARY OF THE INVENTION

The above and other objects are achieved by an aqueous composition for the manufacture of acid resistant hard pharmaceutical capsules, characterized in that it comprises (i) an aqueous solvent, (ii) gellan gum and (iii) one or more water soluble, film forming polymers, wherein the weight ratio of gellan gum to said one or more water soluble, film forming polymers is between 4/100 to 15/100, lower and upper limits included.

The above and other objects are also achieved by an acid resistant hard pharmaceutical capsule shell comprising (I) moisture, (II) gellan gum and (III) one or more water soluble film forming polymers, wherein the weight ratio of gellan gum to said one or more water soluble film forming polymers is between 4/100 to 15/100, lower and upper limits included.

The above and other objects are also achieved by an acid resistant hard pharmaceutical capsule comprising a shell as defined above.

The above and other objects are also achieved by an acid resistant hard pharmaceutical capsule comprising a shell as defined above, wherein said shell is filled with one or more acid-instable substances and/or one or more substances associated with gastric side effects in humans and/or animals.

The above and other objects are also achieved by a dip-molding process for the manufacture of an acid resistant hard pharmaceutical capsule shell, said process comprising the steps of:

(a) dipping pins into an aqueous composition as defined above
(b) withdrawing the dipping pins from the aqueous composition and
(c) drying the composition adhered on the dipping pins so as to obtain a shell;

wherein the steps (a) to (c) are performed in the order in which they are presented.

The above and other objects are also achieved by the use of an aqueous composition as defined above for the manufacture of acid resistant hard pharmaceutical capsule shells and capsules.

The above and other objects are also achieved by the use of an acid resistant hard pharmaceutical capsule shell for the manufacture of a medicament for the administration to a human or an animal being of one or more acid-instable substances and/or one or more substances associated with gastric side effects in humans and/or animals.

DETAILED DESCRIPTION OF THE INVENTION

In the current invention, unless otherwise indicated, "hard capsule" means a conventional hard pharmaceutical capsule intended for oral administration to a human or animal being, said capsule consisting of two co-axial, telescopically-joined parts, referred to as body and cap. Normally, caps and bodies have a side wall, an open end and a closed end. The length of the side wall of each of said parts is generally greater than the capsule diameter. The capsule caps and bodies are telescopically joined together so as to make their side walls partially overlap and obtain a hard capsule shell. "Partially overlap" also encompasses an embodiment wherein the side walls of caps and bodies have substantially the same length so that, when a cap and a body are telescopically joined, the side wall of said cap encases the entire side wall of said body. Thus, the hard capsules of the present invention do not structurally depart from the conventional definition of hard capsules. Generally, "capsule" refers to both empty and filled capsules whereas "shell" specifically refers to an empty capsule. In case the hard capsule shells are filled with substances in liquid form, it is intended that the hard capsules of the invention may be sealed or banded according to conventional techniques to avoid leakage of contained substances.

In the current invention, acid resistance is tested using the apparatus and procedure disclosed in the disintegration test for dosage forms of USP-30 (essentially, simulated gastric fluid TS, at 37±2° C. in a basket/rack assembly). Unless otherwise indicated, "acid resistance" or "acid resistant" means that when subjected to the USP disintegration test, the hard capsule shells and capsules of the invention do not present leaks for at least 1 hour.

The capsule shells and capsules of the invention also display satisfactory dissolution properties in simulated intestinal fluid at pH 6.8, 37±2° C., in a paddle apparatus. Dissolution profile of an exemplary capsule of the invention in simulated gastric and intestinal fluids is disclosed in the examples and FIG. 1. When tested in the dissolution test as disclosed in the Japanese Pharmacopoeia 2 (JP2), the hard capsules of the invention met the definition of enteric resistant hard capsules contained therein.

In the current invention, unless otherwise indicated, "aqueous solvent" preferably means water, more preferably deionised water, more preferably "aqueous solvent" consists of deionised water. The aqueous composition of the invention is thus a composition obtained by adding at least gellan gum and one or more water soluble, film forming polymers in mutual amounts as defined herein to an aqueous solvent. For the same reason, in the present invention, unless otherwise indicated moisture is interchangeably used with water, In the current invention, unless otherwise indicated, "acid-instable substances" refers to substances or compositions in any physical form, preferably solid or liquid pharmaceutical drugs or pharmaceutical compositions intended for human or animal oral administration, that are chemically or physically, partially or totally, decomposed by an acid environment, wherein acid environment preferably means a gastric environment simulated in vitro by dissolution media having a pH of about 1.2.

In the current invention, unless otherwise indicated, "one or more substances associated with gastric side effects in humans and/or animals" refers to substances or compositions, preferably pharmaceutical drugs or compositions intended for human or animal oral administration, whose release in the stomach upon oral administration to a human or animal being is associated to gastric side-effects, such as gastric reflux or impairment of physiological and/or structural integrity of gastric mucosa (e.g. stomach ulcers).

In one aspect, the present invention relates to aqueous composition for the manufacture of acid resistant hard pharmaceutical capsules, characterized in that it comprises (i) an aqueous solvent, (ii) gellan gum and (iii) one or more water soluble, film forming polymers, wherein the weight ratio of gellan gum to said one or more water soluble, film forming polymers is between 4/100 to 15/100, lower and upper limits included.

In a preferred embodiment, the aqueous composition of the invention consist of (i) an aqueous solvent, (ii) gellan gum and (iii) one or more water soluble, film forming polymers, wherein the weight ratio of gellan gum to said one or more water soluble, film forming polymers is between 4/100 to 15/100, lower and upper limits included.

The one or more water soluble film forming polymers contained in the aqueous composition of the invention (ingredient (iii)) preferably represent the main constituent by weight of final capsule shells. The use of water soluble polymers in dip molding manufacturing process of hard pharmaceutical capsules is already known to the public and widely disclosed in many publications and patents. The water soluble film forming polymers presently used are all commercially available.

In one embodiment, the one or more water soluble film forming polymers are selected from the group consisting of cellulose derivatives, preferably HPMC; gelatine, pullulan, PVA and starch derivatives, preferably hydroxypropyl starch. In a preferred embodiment, the film forming polymers are selected from the group consisting of HPMC; gelatine, pullulan, PVA and hydroxypropyl starch as they form films with optimal mechanical performance in terms of elastic module and brittleness. In a particularly preferred embodiment, the film forming polymers comprise HPMC and/or gelatin. In an even more preferred embodiment, the film forming polymers consist of HPMC. In an even more preferred embodiment, the film forming polymers consist of gelatin. Suitable types of HPMC are well-known in the art and an example is HPMC type 2910 (as defined in USP30-NF25). Other less preferred types of HPMC are HPMC 2208 and HPMC 2906 (as defined in USP30-NF25).

Gellan gum is an exopolysaccharide produced by fermentation. In the present invention, gellan gum is used in a ratio of about 4 to 15 parts, preferably about 4.5 to 8 parts, more preferably about 4.5 to 6 parts by weight, lower and upper limits included, per about 100 parts by weight of the one or more water soluble film forming polymers. In a different embodiment of the invention, gellan gum is used at a ratio of about 5 or 5.5 parts by weight per about 100 parts by weight of the one or more water soluble film forming polymers. Upon experimental evidence, It is believed that if lower amounts of gellan gum are used, the final hard capsules do not have enough acid resistance under disintegration test at pH 1.2, whereas higher gellan content, at process conditions (e.g. T and solid content) typical of conventional non-thermogelling dip-moulding techniques (for conventional processes, see e.g. the patent literature reported above), may cause excessive viscosity and excessive gelling ability of the aqueous composition thus making it impossible to manufacture the capsules at the requested high speed and quality. The preferred values of gellan to polymer ratio are believed to optimally combine the technical effects achieved by the present invention and processability aspects.

Due to its gelling properties, gellan gum is a typical component of setting systems conventionally used in the manufacture of immediate release hard capsules when the water soluble film forming polymers used, contrary to gelatin, do not present per se satisfactory gelling properties (e.g. HMPC or modified starches). However, in the prior art, gellan gum is used in amounts by weight which are typically very low with respect the weight of the water soluble film forming polymer(s). For example, amounts of gellan gum typically employed are below 1 part by weight per about 100 parts by weight of the water soluble film forming polymer(s), amount which are significantly lower than those used in the present invention, Additionally, gellan gum is often used in combination with so-called gelling aids (typically salts of Na+, K+ or Ca2+). The use of low amounts of gellan gum and its combination with gelling aids are taught to fully respond to the need of making the main film forming polymer to gel on dipping pins and obtain suitable hard capsule shells.

Now, Applicant has found that by working within the ratio of gellan gum to water soluble film-forming polymers as indicated above, suitable hard capsules can be obtained and also acid resistance can be imparted to such capsules.

Another remarkable advantage is that the addition of the so-called gelling aids is no longer necessary, even when working with film-forming polymers that, like HPMC, have per se poor gelling properties. In other words, when gellan gum is used in weight ratio indicated above, a composition suitable for the manufacture of hard capsules can be obtained out of HPMC or hydroxypropyl starch aqueous compositions without adding gelling aids (e.g. cations) to the aqueous composition. The optional absence of added gelling aids has an advantageous impact on stability of drugs filled into the final hard capsule shells and hard capsule dissolution profile. The fact that the aqueous composition of the invention does not contain added gelling aids preferably means that it does not contain gelling aids, e.g. cations, in an amount higher than the amount of the same aids that is naturally present in gellan gum. In another embodiment, the fact that the aqueous composition of the invention does not contain added gelling aids preferably means that it contains gelling aids, e.g. cations, in an amount not higher than the amount of the same aids that is naturally present in gellan gum. Such natural amount can be easily established by routine laboratory tests on purchased gellan gum batches or it can be directly provided by gellan gum suppliers.

The hard capsules of the invention do not leak at pH 1.2 in a USP-30 simulated gastric fluid for at least 1 hour, confirming the acid-resistant performance.

Typically, the combined amounts of ingredients (ii) and (iii) (i.e. gellan together with the one or more water-soluble film forming polymers) in the aqueous composition of the invention are between about 10% and 40%, more preferably between about 15% and 25% by weight over the total weight of the aqueous composition. Adapting the appropriate concentration of the film forming polymer to the specific polymer used and the desired mechanical properties of the film is well within the abilities of a skilled person in the field of hard capsules manufacturing.

Optionally, the aqueous composition of the invention can contain at least one inert, non-toxic pharmaceutical grade or food grade pigment such as titanium dioxide, iron oxides and other colouring agents. Generally, 0.001 to 5.0% by weight of pigment can be included in the aqueous composition. The weight is expressed over the total weight of the solids in the aqueous composition.

Optionally, the aqueous composition of the invention can contain an appropriate plasticizer such as glycerine or propylene glycol. To avoid an excessive softness, the plasticizer content has to be low, such as between 0% and 20%, more preferably between 0% and 10%, even more preferably between 0% and 5% by weight over the total weight of the solids in the aqueous composition.

Optionally, the aqueous composition of the invention can contain further ingredients typically used in the manufacture of hard capsules such as surfactants and flavouring agents in amounts known to a skilled person and available in publications and patents on hard capsules In another aspect, the present invention relates to an acid resistant hard capsule shell obtained by using an aqueous composition as defined above. In a particular embodiment, the shell comprises (I) moisture, (II) gellan gum and (III) one or more water soluble film forming polymers, wherein the weight ratio of gellan gum to said one or more water soluble film forming polymers is between 4/100 to 15/100, lower and upper limits included.

In a preferred embodiment, acid resistant hard capsule shell consists of (I) moisture, (II) gellan gum and (III) one or more water soluble film forming polymers, wherein the weight ratio of gellan gum to said one or more water soluble film forming polymers is between 4/100 to 15/100, lower and upper limits included.

Whenever applicable and unless technically incompatible, all the features and preferred embodiments disclosed in connection with the aqueous compositions of the invention are disclosed also in connection with any other aspect of the invention, including the acid resistant hard capsule shells and shells of the invention.

The moisture content of the capsule shells of the invention mainly depends upon the one or more water-soluble film forming polymers used and relative humidity of the environment in which the shells are stocked after production. Typically, the moisture content is between about 2% and 16%, over the total weight of the shell. As an example, under conditions conventionally adopted for storing hard capsules, the hard capsule shells of the present invention contain between about 2-8%, preferably about 2-6%, preferably about 3-6% by weight of moisture over the weight of the shell when the only film forming polymer used is HPMC and 10-16% of moisture over the weight of the shell, when the only film forming polymer used is gelatine.

In another aspect, the present invention relates to an acid resistant hard capsule comprising a shell as defined above.

The capsules of the invention can be obtained by filling the shells of the invention with one or more substances to be encapsulated. Once filled, the capsules can be made tamperproof e.g. by using appropriate banding solution used in the field of hard capsules to make the joint permanent.

In a preferred embodiment, a hard capsule shell of the invention as defined above is filled with one or more acid-instable substances and/or one or more substances associated with gastric side effects in humans and/or animals.

In another aspect, the present invention relates to a dip-molding process for the manufacture of an acid resistant hard pharmaceutical capsule shell, said process comprising the steps of:
  (a) dipping pins into an aqueous composition as defined above
  (b) withdrawing the dipping pins from the aqueous composition and
  (c) drying the composition adhered on the dipping pins so as to obtain a shell;
wherein the steps (a) to (c) are performed in the order in which they are presented.

After drying step (c), the shell obtained can be stripped off the pins and cut to a desired length. In this manner capsule shell parties (bodies and caps) are obtained that subsequently can be telescopically joint so as to form a final empty capsule. In case of filling with liquid substances, and if desired, once filled the capsule can be made tamper-proof by appropriate techniques known in the field such as banding or sealing techniques.

Examples 1-5

The Table 1 below reports the quantitative composition of the aqueous compositions used in examples 1 to 5. Hard pharmaceutical capsule shells were obtained from each composition according to the dip-molding manufacturing process disclosed below (and identical for all examples).

TABLE 1

| Example | 1 | 2 | 3 | 4 | 5 |
|---|---|---|---|---|---|
| Gellan gum/HPMC weight parts ratio | 2.0/100 | 3.0/100 | 4.5/100 | 6.0/100 | 8.0/100 |
| Gellan gum (g) | 20 | 29.4 | 42.5 | 54 | 68 |
| HPMC (g) | 1000 | 980 | 940 | 900 | 850 |
| Deionised water (g) | 4000 | 4020 | 4060 | 4100 | 4100 |
| Total concentration | 20.3 | 20.1 | 19.5 | 18.9 | 18.3 |

Dip-Molding Manufacturing Process

In a reactor of 7.5 liters capacity, the deionized water was heated up to 75° C. The gellan gum and HPMC (type of 2910, viscosity grade of 6 cPs at 2% aqueous solution at 20° C.) in powder form were mixed together. The powder blend was then dispersed in the water at 75° C. under stirring. Stirring was kept on till complete dissolution of the gellan gum. After de-bubbling of the solution under very gentle stirring, the solution was then equilibrated at 60° C.

The obtained solution was transferred in a dipping dish of a pilot machine of conventional hard gelatine capsule production equipment. While keeping the dipping solution at 60° C., natural transparent hard capsule shells of size 0 with the same dimension specifications to the conventional hard gelatine capsules were produced by dip moulding.

The obtained capsule shells were firstly filled with a mixture of lactose and Indigotine (FD&C blue N° 2) 0.1% by weight over the total weight of the mixture, and then banded with solution of shellac in alcohol. The banding served to avoid the capsule body and cap separation during the disintegration test at pH 1.2.

The filled and banded capsules were tested according to USP-30 disintegration test in the USP-30 simulated gastric fluid (pH 1.2, without enzyme) for the assessment of the acid resistance. The results reported in Table 2 (below) clearly support the resistance to acidic conditions of the hard capsules of the invention.

TABLE 2

| | Example | | | | |
|---|---|---|---|---|---|
| | 1 | 2 | 3 | 4 | 5 |
| USP disintegration of capsules at 37 ± 2° C. and pH 1.2 | | | | | |
| First leak time (min) | 21 | 24 | No leaks after 1 hour | | |

Example 6

An aqueous composition was obtained following the process disclosed above for examples 1-5 but starting from 5 kg gellan gum and 100 kg HPMC (gellan gum/HPMC=5/100) into 480 liters of deionised water at 75° C. in an industrial scale vessel.

After complete gellan gum dissolution, de-bubbling and equilibration, the aqueous composition was transferred in a dipping dish of a conventional hard gelatine capsule production line at industrial scale. While keeping the solution temperature at 60° C., 400000, size 0 capsules were produced by dip moulding process. The process conditions were adjusted so as to obtain hard capsules in the same dimension specifications of conventional hard gelatine capsules.

The obtained capsules were tested on an industrial scale filling equipment GKF, which confirmed a good filling performance, similar to conventional hard gelatine capsules.

The capsules were filled with acetaminophen (APAP), and then banded as described in examples 1-5.

The disintegration test at pH 1.2 as disclosed for examples 1-5 revealed no visual leaks after 1 hour in the simulated gastric fluid. The dosing of the dissolved APAP in the disintegration medium after 1 hour revealed only 7.9% APAP dissolved (presumably due to a minor APAP diffusion through the shell.) These results confirmed the capsule good structural resistance in acid medium.

Dissolution Test

The same hard capsules of example 6 were placed in a paddle apparatus and tested according to the dissolution test for dosage forms as described in Japanese pharmacopeia 2 (JP2). The capsules underwent dissolution at 50 rpm by using in sequence the simulated gastric fluid (pH 1.2) and intestinal fluid (pH 6.8) disclosed in the JP2. The results of dissolution test are reported in FIG. 1. The results show that the dissolution profile of the hard capsules of the invention meets the definition of enteric release hard capsules according to the JP2.

The invention claimed is:

1. An acid resistant hard pharmaceutical capsule shell consisting essentially of gellan gum, HPMC, and optionally at least one additive selected from the group consisting of inert, non-toxic pharmaceutical grade or food grade pigments, plasticizers, surfactants, and flavouring agents, wherein the weight ratio of gellan gum to HPMC ranges from 4.5 to 15 parts by weight of gellan gum per 100 parts by weight of HPMC, wherein said hard capsule shell exhibits resistance to leakage of at least 1 hour at pH 1.2 in a USP-30 simulated gastric fluid, and further wherein the capsule shell is filled with at least one substance selected from the group consisting of acid-instable substances and substances associated with gastric side effects in humans and/or animals.

2. The hard capsule shell according to claim 1 further wherein the capsule shell has a moisture content ranging from about 2% to about 16% over the total weight of the shell.

3. A dip-molding process for the manufacture of an acid resistant hard pharmaceutical capsule shell according to claim 1, said process comprising:
   dipping pins into an aqueous composition according to claim 1;
   withdrawing the dipping pins from the aqueous composition; and
   drying the composition adhered on the dipping pins so as to obtain a shell.

4. A method of administering to a patient in need the acid resistant hard pharmaceutical capsule shell according to claim 1, wherein the acid resistant hard pharmaceutical capsule contains at least one substance selected from the group consisting of acid-instable substances and substances associated with gastric side effects.

* * * * *